United States Patent
Herczeg et al.

(10) Patent No.: US 12,220,664 B2
(45) Date of Patent: Feb. 11, 2025

(54) PERFUSION FILTRATION SYSTEM

(71) Applicant: WaterSep BioSeparations LLC, Marlborough, MA (US)

(72) Inventors: Attila Herczeg, Southborough, MA (US); Julie-Anne Burdick, Hudson, MA (US)

(73) Assignee: WaterSep Bioseparations LLC, Marlborough, MA (US)

( * ) Notice: Subject to any disclaimer, the term of this patent is extended or adjusted under 35 U.S.C. 154(b) by 0 days.

(21) Appl. No.: 18/456,320

(22) Filed: Aug. 25, 2023

(65) Prior Publication Data

US 2023/0405528 A1 Dec. 21, 2023

Related U.S. Application Data

(63) Continuation of application No. 16/813,656, filed on Mar. 9, 2020, now Pat. No. 11,772,048.

(51) Int. Cl.
| | |
|---|---|
| *B01D 63/00* | (2006.01) |
| *B01D 63/02* | (2006.01) |
| *B01D 63/04* | (2006.01) |
| *B01D 65/00* | (2006.01) |
| *C12M 1/00* | (2006.01) |
| *C12M 1/34* | (2006.01) |
| *D01F 1/08* | (2006.01) |

(52) U.S. Cl.
CPC ....... *B01D 63/043* (2013.01); *B01D 63/0241* (2022.08); *B01D 65/00* (2013.01); *C12M 23/26* (2013.01); *C12M 29/10* (2013.01); *C12M 41/40* (2013.01)

(58) Field of Classification Search
None
See application file for complete search history.

(56) References Cited

U.S. PATENT DOCUMENTS

| | | | |
|---|---|---|---|
| 6,544,424 B1 | 4/2003 | Shevitz et al. | |
| 2006/0201876 A1 | 9/2006 | Jordan | |
| 2007/0163942 A1* | 7/2007 | Tanaka | C02F 1/444 210/321.89 |
| 2014/0093952 A1 | 4/2014 | Serway | |
| 2016/0194589 A1 | 7/2016 | Liderfelt et al. | |
| 2017/0292103 A1 | 10/2017 | Cattaneo et al. | |
| 2019/0070564 A1 | 3/2019 | Love et al. | |

(Continued)

FOREIGN PATENT DOCUMENTS

| | | |
|---|---|---|
| KR | 100638322 B1 | 10/2006 |
| KR | 20130124634 A | 11/2013 |

(Continued)

OTHER PUBLICATIONS

Castilho et al., "An integrated process for mammalian cell perfusion cultivation and product purification using a dynamic filter," *Biotechnology Progress* 18(4): 776-781, 2002.

(Continued)

*Primary Examiner* — Allison G Fitzsimmons
(74) *Attorney, Agent, or Firm* — Klarquist Sparkman, LLP

(57) ABSTRACT

Disclosed herein is a perfusion filtration module or bioreactor for filtering a fluid, wherein the filtration module or bioreactor has a plurality of hollow fiber filter membranes that are splayed to reduce fouling of the filtration array.

16 Claims, 6 Drawing Sheets

(56) References Cited

U.S. PATENT DOCUMENTS

2019/0314567 A1     8/2019    Straube et al.

FOREIGN PATENT DOCUMENTS

| WO | WO 01/59061 | 8/2001 |
|---|---|---|
| WO | WO 2018/183971 | 10/2018 |

OTHER PUBLICATIONS

Chapman LAC, Shipley RJ, Whiteley JP, Ellis MJ, Byrne HM, et al. (2014) Optimising Cell Aggregate Expansion in a Perfused Hollow Fibre Bioreactor via Mathematical Modelling. PLoS One 9(8): e105813. doi: 10.1371/journal.pone.0105813.

Conversion of Bioreactors to Continuous Perfusion Using Hollow Fiber Cell Separators Practical Aspects Spectrum Laboratories Retrieved Dec. 31, 2019.

Davis et al., "Modeling perfusion at small scale using ambr15TM," 2015.

International Search Report and Written Opinion, mailed May 7, 2021, issued for International Patent Application No. PCT/US2021/020504, 7 pages.

Menshutina et al., "Modelling of hollow fiber membrane bioreactor for mammalian cell cultivation using computational hydrodynamics," *Bioprocess and Biosystems Engineering* 43: 549-567, Mar. 2020.

Tapia et al., "Bioreactors for high cell density and continuous multi-stage cultivations: options for process intensification in cell culture-based viral vaccine production," *Applied Microbiology and Biotechnology* 100: 2121-2132, Mar. 2016.

Vermasvuori et al., "Economic comparison of diagnostic antibody production in perfusion stirred tank and in hollow fiber bioreactor processes," *Biotechnology Progress* 27(6): 1588-1598, Nov. 2011.

Walther et al., "The effects of alternating tangential flow (ATF) residence time, hydrodynamic stress, and filtration flux on high-density perfusion cell culture," *Biotechnology and Bioengineering* 116(2): 320-332, Feb. 2019.

Wang et al., "Larger pore size hollow fiber membranes as a solution to the product retention issue in filtration-based perfusion bioreactors," *Biotechnology Journal* 14(2): 1800137, Feb. 2019.

\* cited by examiner 201 202 203 204

PERFUSION FILTRATION SYSTEM

CROSS REFERENCE TO RELATED APPLICATION

This application is a continuation of U.S. patent application Ser. No. 16/813,656, filed Mar. 9, 2020. The prior application is incorporated by reference.

FIELD

Embodiments of this disclosure relate generally to process filtration systems, and more particularly to membrane bioreactor systems and other devices utilizing perfusion in hollow fiber filtration.

BACKGROUND

Biomanufacturing employs biological systems to produce commercially important biomaterials and biomolecules used in the fields of medicine, consumer goods and industrial processes. Illustrative examples of biomanufactured products include, but are not limited to, active pharmaceuticals; monoclonal antibodies; vaccines; proteins; amino acids; enzymes; animal cells, tissues and replacement organs; biofuels; biochemicals; and 'green' products to replace petroleum-derived chemicals. Regardless of scale, biomanufacturing generally uses fluid mixtures that require purification, which frequently involve one or more filtration steps.

Continuous biomanufacturing is gaining popularity as a more efficient way of producing solutions or suspensions of the target species. Of particular interest are "single pass" processes, wherein the retained materials or the filtered materials, as the case may be, are at or slightly above the desired concentration of the target solute after the first pass such that there is no need for recirculation and/or further purification.

Certain methods of manufacturing biologically-produced products involve continuously-operated bioreactors, such as perfusion bioreactors and chemostats. Under substantially continuous operation of a bioreactor, a portion of the contents of the bioreactor may be pumped out of the bioreactor through one or more filters.

For example, cell culture has been of interest in recent years because of the revolution in biotechnology and genetic engineering. Cultured cells are engineered to make proteins, receptors, vaccines, antibodies and other biologically derived substances for therapy, research, and diagnostics. Processes may be operated in a batch mode, where a bioreactor is seeded with a small number of cells and the cells are grown to a higher density. The cells secrete the product of interest and eventually die due to lack of nutrients. The culture is harvested and the target product purified.

On the other hand, perfusion mode operation, wherein filtration occurs from the outside-in such that the permeate flows into the lumen of a filter fiber, for example, can offer better economics and faster cycle times. In perfusion mode, cells are retained in the bioreactor, and the product is removed in a controlled fashion along with metabolic byproducts that may be toxic to further cell growth. In perfusion mode, a feed-stream comprising nutrients and other components is added continually, while concentrations are optionally monitored to achieve optimum yield. A perfusion mode operation is capable of achieving high cell densities and long cell life such that the cultured cells are maintained in a highly productive state for weeks or months. Perfusion mode offers the advantages of more efficient use of nutrients, less buildup of toxic metabolic byproducts that would inhibit product formation and a more uniform nutrient distribution throughout the bioreactor, allowing more efficient use of cells. Thus, it is possible to achieve higher yields from smaller reactors, compared to batch mode operation, thereby providing considerable cost savings. Moreover, product streams are generally cell-free, eliminating the need for a cell separation step.

Hollow fiber filtration is frequently the method of choice in perfusion operations because of the large surface area provided by the hollow fibers filters. However, filtration methods require some means to keep the filter from clogging over the required time of operation. Filter membranes can foul or clog; thus reducing the rate of filtration, as cells and/or other debris coat the individual fibers. Eventually, the entire fiber bundle may be engulfed as shown in FIG. 1, such that no permeate is able to pass through the filter into the lumen.

Various attempts have been made to keep cells and cell debris from fouling filter bundles. For example, in United States Patent Application No. US20170292103 to Cattaneo et al., cross-flow filters containing hollow fiber membranes are operated with high tangential liquid velocity in order to keep the fiber surfaces clean. However, such operation places limits on the level of control needed to produce optimum yield. Moreover, high tangential velocity operation, by itself, is generally ineffective in preventing or, at least, mitigating the engulfing of the entire fiber bundle, and high shear resulting from operating fouled systems using increasing trans-membrane pressures may result in cell breakage and loss of yield.

In another example, an alternating tangential flow system U.S. Pat. No. 6,544,424 to Shevitz discloses how alternating tangential flow (ATF) mode may be used to enable the growth of mammalian cells to a high density without incurring the shear caused by standard tangential flow equipment which normally results in cell breakage and loss of yield. However, once the fiber bundle has become engulfed by cells and/or debris, alternating tangential flow by itself, will be ineffective in dislodging the engulfing cells and/or debris.

Therefore there remains a need for a filtration system that will prevent or mitigate the engulfing of the entire bundle when operating systems with high solid density. This need, inter alia, is addressed by the apparatus disclosed herein.

BRIEF DESCRIPTION OF THE DRAWINGS

In FIG. 3(a) the hollow fiber filter membranes are bundled such that they are in close proximity to one another. In FIG. 3(b) the hollow fiber filter membranes are splayed such that there is a larger interstitial distance between neighboring fibers.

The drawings are not necessarily to scale and no such intention should be inferred. Moreover, the shapes of the potting and mounting blocks are not intended to be limited as depicted, but as in the claims attached hereto.

DETAILED DESCRIPTION

Figure 1:
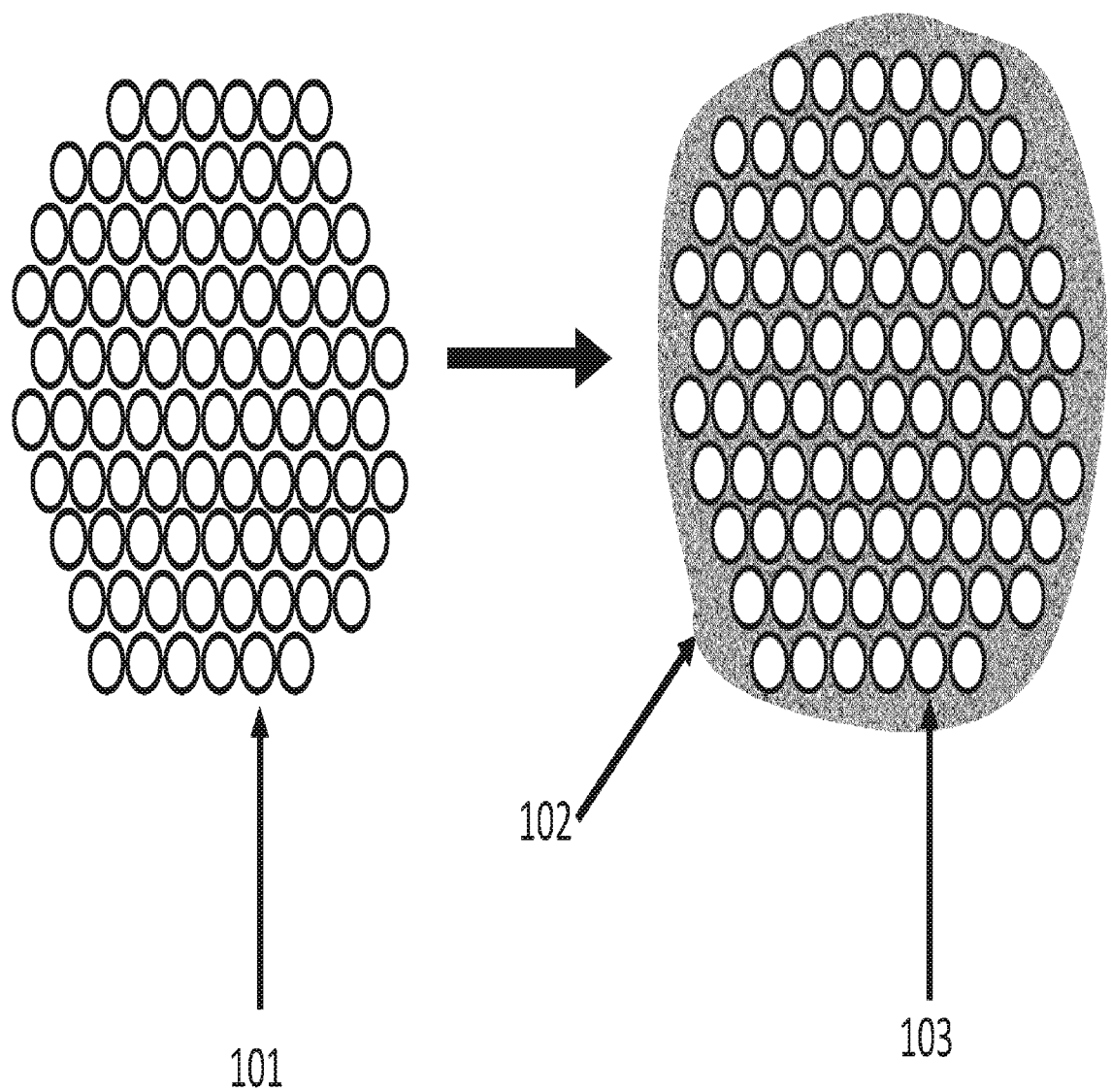
FIG. 1 depicts a cross sectional rendering of a filter bundle, operating in perfusion mode, being engulfed by cells and/or other debris.

FIG. 1 depicts a cross sectional rendering of a hollow fiber filter bundle 101, operating in perfusion mode, being engulfed by cells and/or other debris 102, such that there is little or no flow of the bioreactor fluid between the hollow fiber filters, exemplified by 103.

Figure 2:
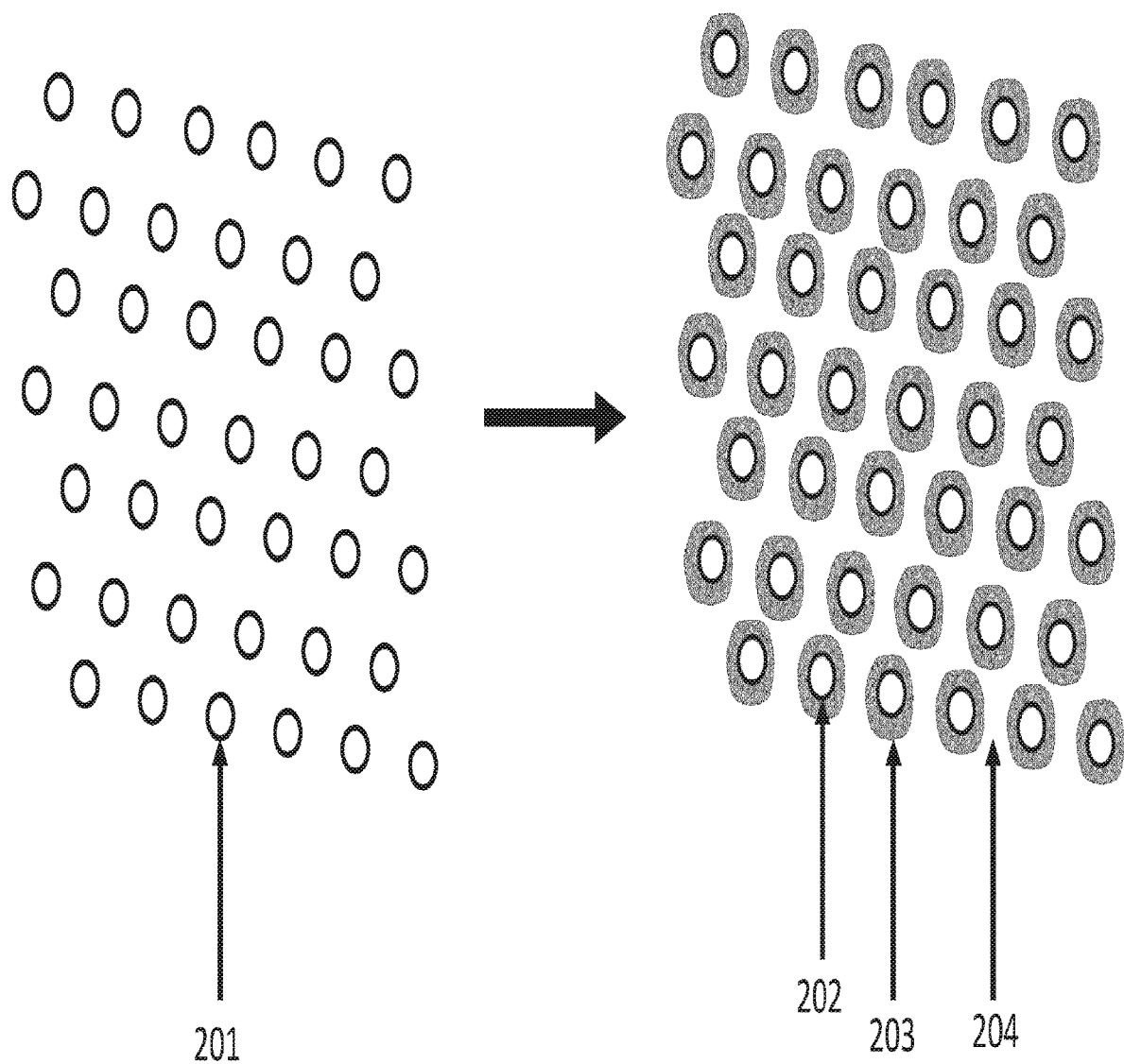
FIG. 2 depicts a cross sectional rendering of a filter bundle, operating in perfusion mode, wherein the filter fibers are separated such that they are not engulfed by cells and/or other debris; thus providing interstitial space that facilitates fluid flow between the fibers.

FIG. 2 depicts a cross sectional rendering of a hollow fiber filter bundle 201, operating in perfusion mode, wherein the filter fibers exemplified by 202 are separated such that they are not engulfed by cells and/or other debris exemplified by 203; thus providing interstitial space 204 that facilitates fluid flow between the hollow filter fibers, even in circumstances where the individual fibers may be coated with cells and debris.

Figure 3:
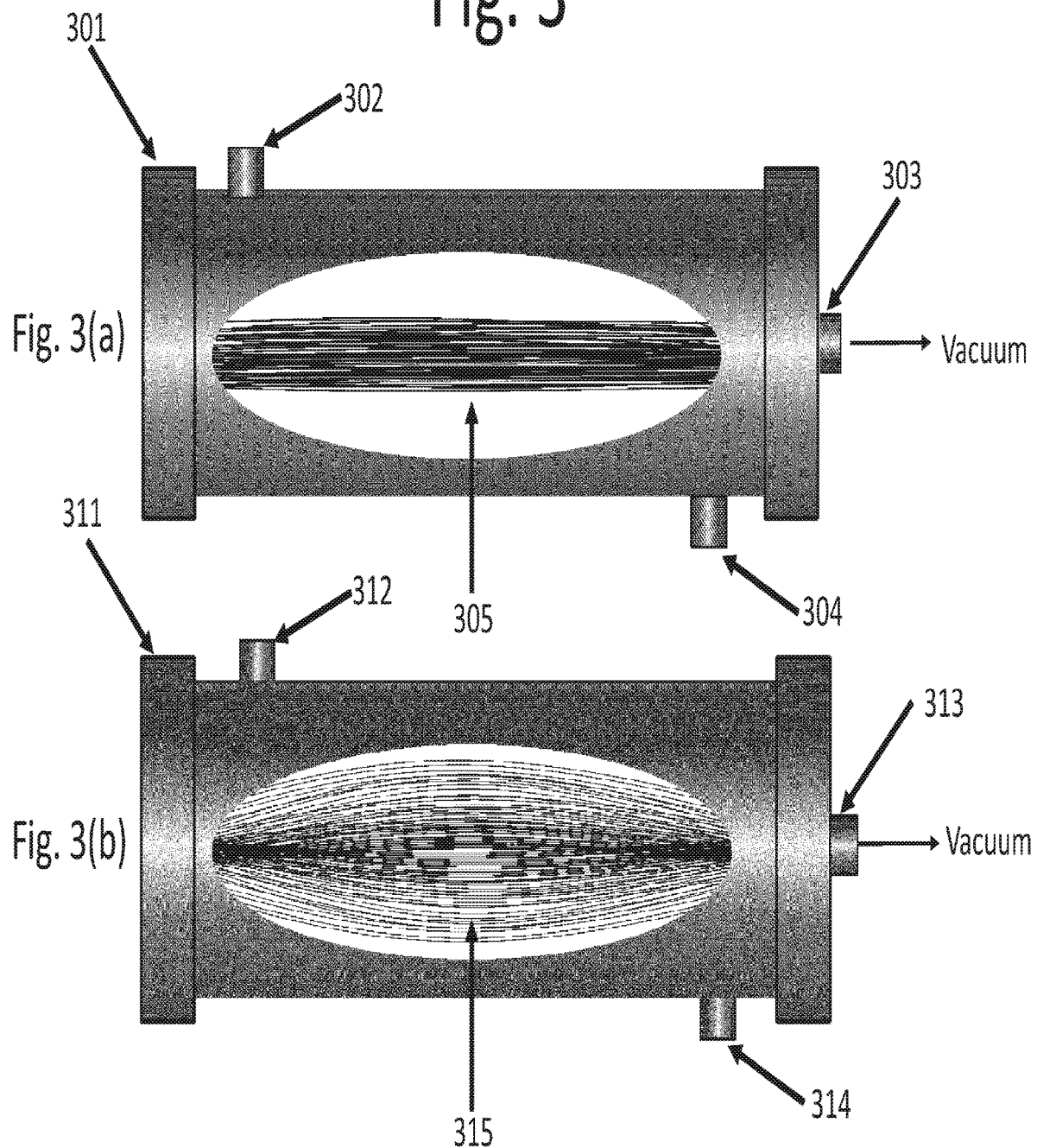
FIG. 3 depicts cutaway renderings of filter modules or compact bioreactors, each having a plurality of hollow fiber filter membranes.

FIG. 3 depicts cutaway renderings of filter modules or compact bioreactors, each having a plurality of hollow fiber filter membranes. In FIG. 3(a) the filter module or bioreactor 301 comprises an inlet port 302, an optional additional port 304 that may be used as an additional inlet port or an exhaust port, and an exit port 303 for removing permeate. The hollow fiber filter membranes 305 are bundled such that they are in close proximity to one another. In FIG. 3(b) the filter module or bioreactor 311 comprises an inlet port 312, an optional additional port 314 that may be used as an additional inlet port or an exhaust port, and an exit port 313 for removing permeate. The hollow fiber filter membranes 315 are splayed such that there is a larger interstitial distance between neighboring fibers.

Figure 4:
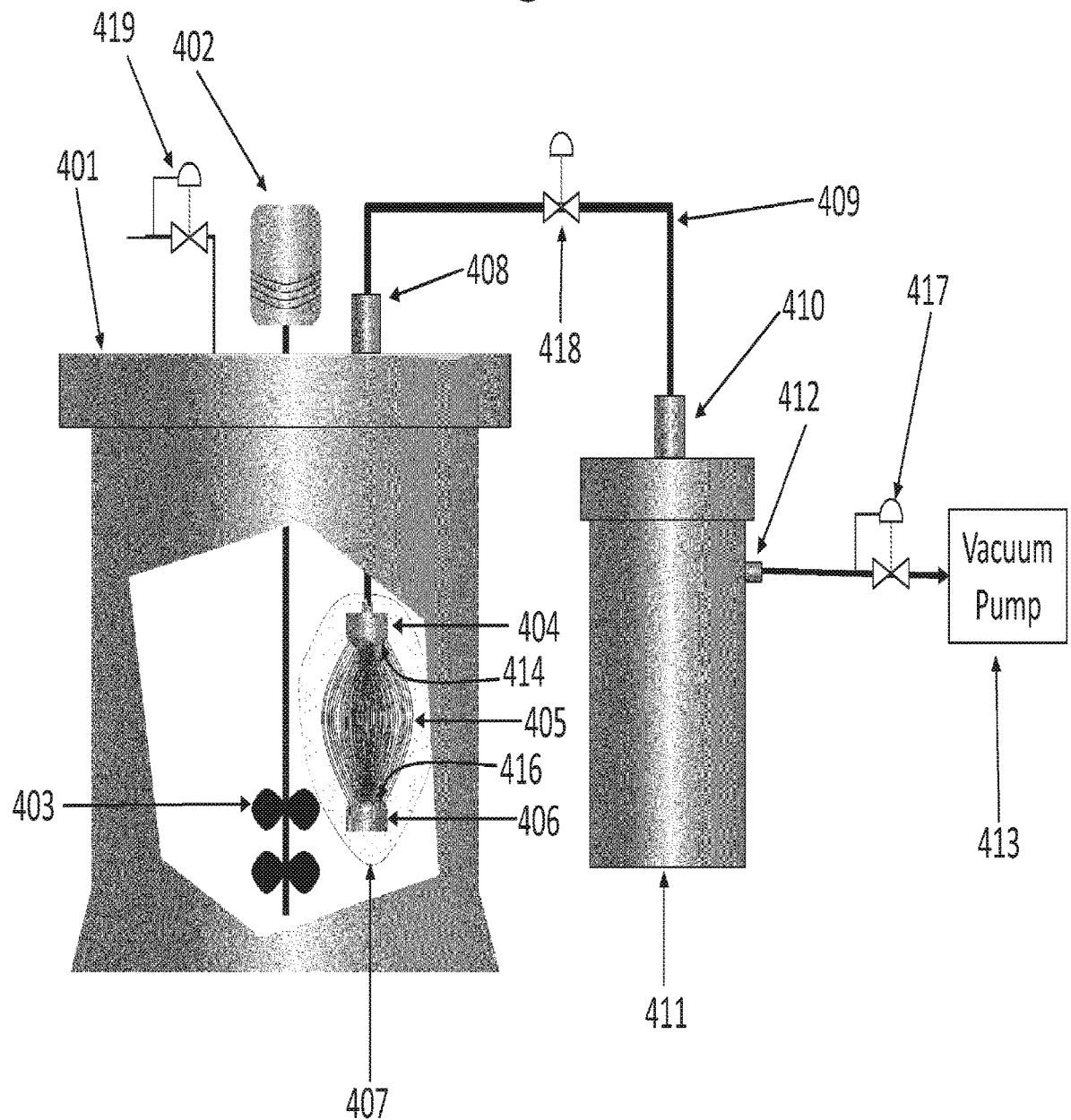
FIG. 4 depicts a large bioreactor having a stirring motor and stirring blades, as well as a filtration module, having a plurality of hollow fiber filter membranes, wherein the hollow fiber filter membranes are splayed to facilitate fluid flow between the fibers. Also shown is a collection vessel to collect permeate extracted from the bioreactor.

FIG. 4 depicts a large bioreactor 401 having a stifling motor 402 and stirring blades 403, as well as a filtration module, comprising a plurality of hollow fiber filter membranes 405, wherein the hollow fiber filter membranes are splayed to facilitate fluid flow between the fibers. The hollow fiber filter membranes 405 are potted into a manifold 404 to allow permeate to flow to the collection vessel via tube 409. Additionally, the manifold 404 is shaped as a cone where the hollow fiber filters emerge to reduce strain in the splayed configuration. The hollow fiber filter membranes 405 are mounted into a mounting block 406 such that they are sealed. Additionally, the mounting block 406 is shaped as a cone 416 where the hollow fiber filters emerge to reduce strain in the splayed configuration. The filter module is enclosed in a protective sack 407. Also shown is a collection vessel 411 to collect permeate extracted from the bioreactor 401. Permeate is transferred from the filter assembly in the bioreactor via tube 409, through inlet port 410. Fluid flow may be urged by a vacuum supplied by vacuum pump 413, applied at vacuum port 412, or by a pump installed in tube 409 (not shown). Flow may be controlled by controlling the vacuum, using one or more pressure control valves such as at 417 and/or one or more flow control valves such as at 418. Within the reactor, pressure may be regulated using pressure control valve 419.

Figure 5:
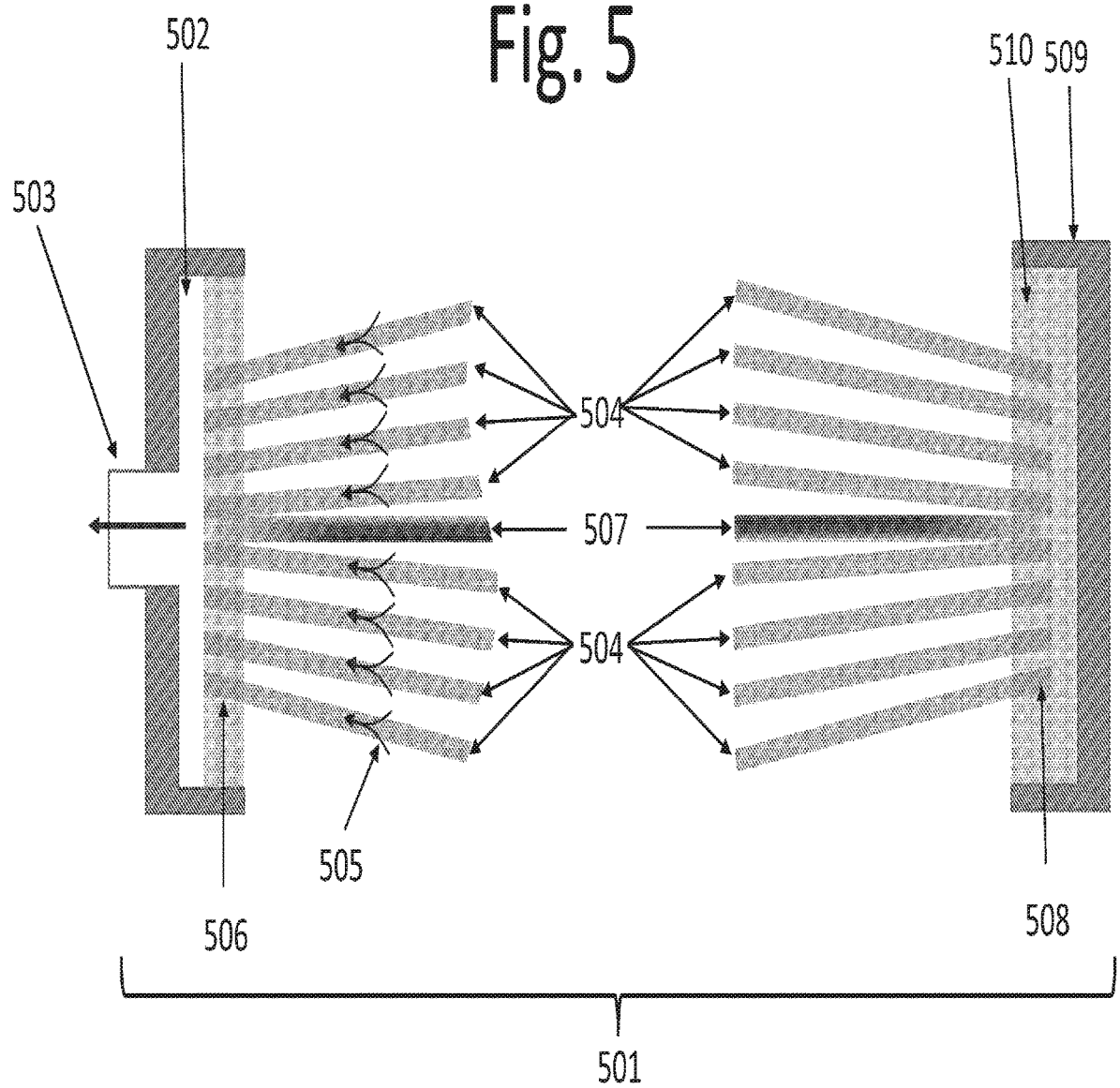
FIG. 5 depicts a cutaway view of a filtration module or compact bioreactor having a plurality of hollow fiber filter membranes, wherein the hollow fiber filter membranes are splayed to facilitate fluid flow between the fibers. At one side, the hollow fiber filter membranes are potted, such that the permeate may be urged out of the module. On the other side, the fibers are mounted such that they are sealed.

FIG. 5 depicts a cutaway, chopped view of a filtration module 501 or compact bioreactor having a plurality of hollow fiber filter membranes 504, wherein the hollow fiber filter membranes are splayed to facilitate fluid flow between the fibers. At one side, the hollow fiber filter membranes are potted 506, such that permeate may be urged out of the module via manifold 502 and exit port 503. On the other side, the fibers are mounted 506 in a mounting block 510 and the mounting block is secured to an end piece 509 such that the hollow fiber filter membranes are sealed. Permeate enters the lumens of the hollow fiber filter membranes as depicted by 505 and flows to the manifold. A rod 507 holds the ends such that the hollow fiber filters may be in a splayed configuration.

Figure 6:
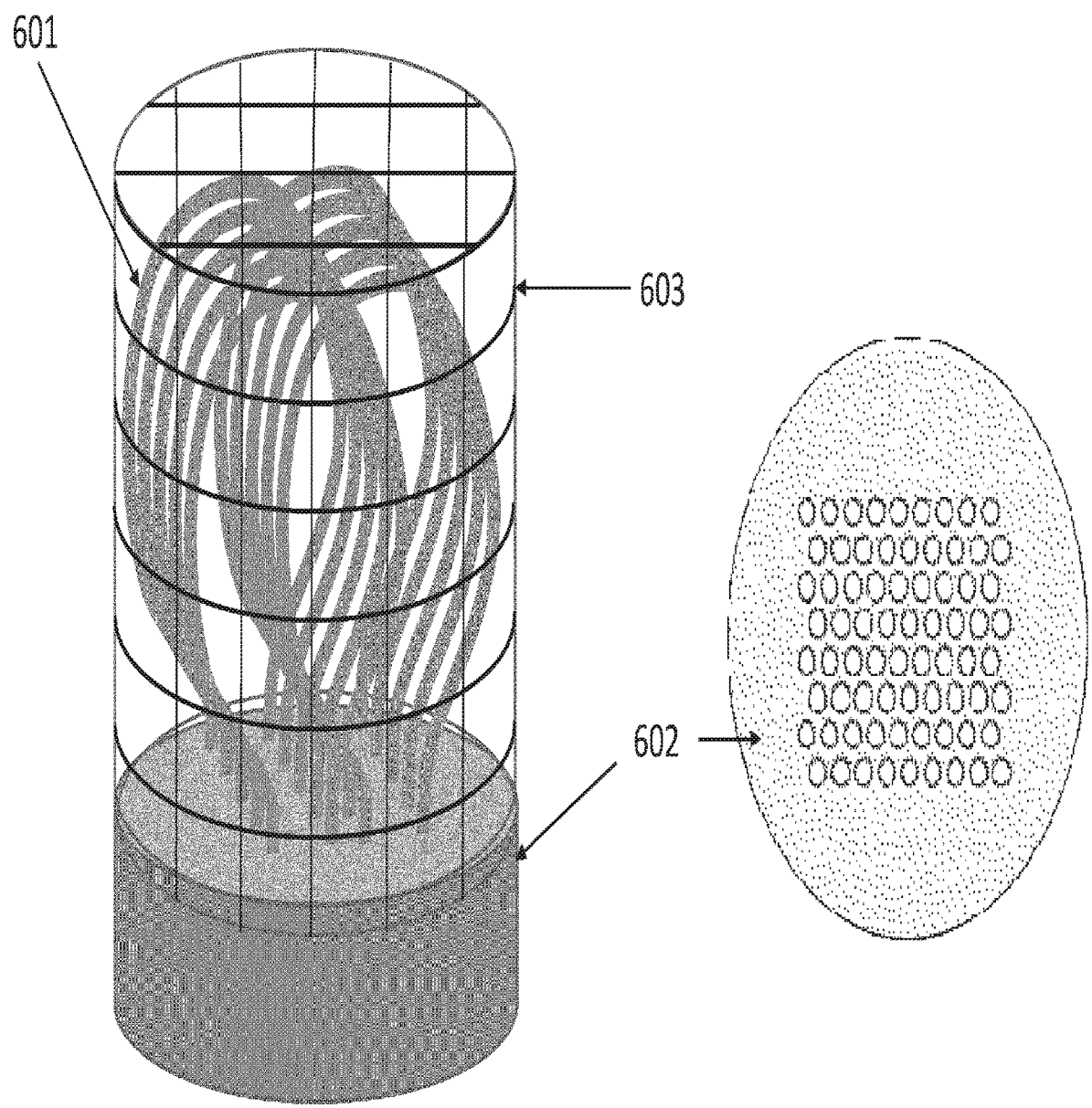
FIG. 6 depicts a cutaway view of a filtration module or compact bioreactor having a plurality of hollow fiber filter membranes, wherein the hollow fiber filter membranes are splayed to facilitate fluid flow between the fibers. In the embodiment shown, fibers are potted at both ends in the same potting block such that they form a loop.

FIG. 6 depicts a view of a filtration module having a plurality of hollow fiber filter membranes 601, wherein the hollow fiber filter membranes are splayed to facilitate fluid flow between the fibers. In the embodiment shown, fibers are potted at both ends in the same potting block 602 and manifold (not shown) such that they form a loop. The assembly is protected from mechanical damage by a cage 603.

More elaborate manifolds such as those known in the art can be used without departing from the scope of the claims appended hereto. For example, some manifolds fitted to cross flow filter cartridges permit series filtration in order to increase capacity or reduce pressures.

DETAILED DESCRIPTION

As used herein, the conjunction "and" is intended to be inclusive and the conjunction "or" is not intended to be exclusive unless otherwise indicated or required by context. For example, the phrase "or, alternatively" is intended to be exclusive. As used herein, it is intended that the terms "cross flow filtration" and "tangential flow filtration" are synonymous. As used herein, the term "exemplary" is intended to point to an example but is not intended to indicate preference. As used herein, the term "about" is understood as within a range of normal tolerance in the art, for example within 2 standard deviations of the mean. For example, the deviation from the nominal value modified by the term "about" may be due to limitations imposed by hardware such as fittings, mounting fixtures, securing structures and the like. "About" can further be understood as being within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about." As used herein, a "filtration system" is understood to comprise one or more filtration modules and may further comprise pumps, valves and other ancillary equipment. As used herein, a "filtration module" is understood to comprise one, two or more filtration segments, fluidly connected as prescribed. As used herein, the terms "upstream" and "downstream" depend on the direction of flow across the filter membrane. For example, in perfusion flow, fluid flows from the outside ("upstream") to the inside ("downstream") of the fiber filter membrane. The terminology is reversed during backflushing.

As used herein, a component is said to be fluidly connected to another component regardless of whether there are control devices between the two components. Control devices include pumps, valves, restrictors, pressure or volume regulators or the like.

As used herein, the term "substantially equal" is used with the understanding that minor errors in the concentration of the retained solute of interest at some stage in filtration may be adjusted during subsequent filtration or additions of solvent to provide more accurately the desired concentration. Accordingly, if it is said that the one quantity of fluid is substantially equal to another, a concentration tolerance of +/−15% would not depart from the scope of the invention. Further, it should be understood that the examples are not limiting in that regard.

As used herein, a point of introduction of a diadiluent may comprise a multi-component module, having any one or all of a reservoir, a fluid output from another process, such as a synthesis module, a blending module for blending one or more solvents and/or one or more solutes, a filtration module, or the like. A point of introduction of a diadiluent may also include one or more control modules for controlling pressure, volumes, temperatures, or the like, including heaters, chillers, pumps having one or more input lines, automatic or manual valves, flow restrictors, active or automated flow controllers or the like.

As used herein, a fluid having dispersed components may be a solution, a stable micellar or colloidal suspension, or a coarser suspension which is stable during a time suitable for its application.

As used herein, the following are understood:

Hollow fiber filter membrane: a hollow fiber with walls comprising a permeable or semi-permeable material, capable of performing a filtration function.

Backwash: reversal of a fluid flow through the filtration media, often as an attempt to clean or "regenerate" a filter, or reduce fouling of the filter during operation.

Permeability: the degree to which a fluid will pass through a permeable body under specified conditions. The space or void volume between molecules allowing fluid flow.

Permeate or filtrate: the fluid which passes through a filter membrane. It is to be understood that the terms, "permeate" or "filtrate" may or may not be used with the accompanying definite or indefinite article. Herein, it is contemplated that the definite article is assumed.

Perfusion: as used herein, the causing of a fluid to flow or be filtered from the outside of a fiber filter membrane into the lumen or inside of a fiber filter membrane.

Retention: the ability of a filter to retain particles (total number or those of a specific size) suspended in a fluid. Retention may be expressed as a percent of particles originally present.

Retentate: that portion of a fluid possibly containing particulate, granular, or globular materials which remains on the upstream side of the filter membrane.

Splay: (verb) to spread the individual members of an array of objects or parts of a single object relative to a substantially collinear compacted array, or other substantially ordered compacted array. Splay: (noun) a splayed configuration. The splay depends on the amount of lineal compression.

Lineal: (adjective) referring to the direction along the length of the non-splayed fiber bundle.

Lateral: (adjective) referring to the direction along a line normal to the lineal direction.

Degree of splay: the relative amount of splay expressed as the ratio of the maximum lateral dimension of the splayed fiber array to the lateral dimension of the fiber array when stretched in its maximum lineal dimension. No splay has a degree of splay equal to 1. A degree of splay greater than 1 indicates a splayed configuration.

Pot, potting, potted: (verb) to embed hollow fiber filter membranes in such a way as to permit flow between the interior of the fiber and the exterior of the embed.

Mount, mounting, mounted: (verb) to embed hollow fiber filter membranes in such a way as to prevent flow between the interior of the fiber and the exterior of the mount.

Feed fluid: the fluid to be filtered through a hollow fiber filter membrane. Without limitation the feed fluid may comprise a liquid, particulates, one or more dissolved components, or a sol.

First and second surfaces: those surfaces from which the potted or mounted hollow fiber filter membranes emerge. In some embodiments, such as shown in FIG. 6, the first and second surfaces may be the same.

Disclosed herein is an embodiment of a perfusion filtration module or bioreactor for filtering a feed fluid, wherein the filtration module or bioreactor has (a) a plurality of hollow fiber filter membranes, each having a first end and a second end, wherein the first ends of the hollow fiber filter membranes are potted, thus forming a first potted end, to enable filtrate flow from the hollow fiber filter membranes, and wherein the second ends of the hollow fiber filter membranes are, either (i) potted, thus forming a second potted end, to enable fluid flow from the hollow fiber filter membranes; or, alternatively, (ii) mounted, thus forming a mounted end, so that the hollow fiber filter membranes are sealed to prevent filtrate flow; (b) a constraint that allows the hollow fiber filter membranes to be held in a splayed configuration when in use, sufficient to permit a feed fluid to flow more freely within the interstitial volume around the outside of the fiber filter membranes, wherein the (i) first potted end and second potted end, or, alternatively, (ii) the first potted end and mounted end have first and second surfaces, respectively, from which the fiber filter membranes emerge.

Further disclosed herein is an embodiment of a perfusion filtration module or bioreactor for filtering a feed fluid, wherein the filtration module or bioreactor has (a) a plurality of hollow fiber filter membranes, each having a first end and a second end, wherein the first ends of the hollow fiber filter membranes are potted, thus forming a first potted end, to enable filtrate flow from the hollow fiber filter membranes, and wherein the second ends of the hollow fiber filter membranes are mounted, thus forming a mounted end, so that the hollow fiber filter membranes are sealed to prevent filtrate flow; (b) a constraint that allows the hollow fiber filter membranes to be held in a splayed configuration when in use, sufficient to permit a feed fluid to flow more freely within the interstitial volume between the individual hollow fiber filter membranes, wherein the first potted end and mounted end have first and second surfaces, respectively, from which the fiber filter membranes emerge.

Further disclosed herein is an embodiment of a perfusion filtration module or bioreactor for filtering a feed fluid, wherein the filtration module or bioreactor has (a) a plurality of hollow fiber filter membranes, each having a first end and a second end, wherein the first ends of the hollow fiber filter membranes are potted, thus forming a first potted end, to enable filtrate flow from the hollow fiber filter membranes, and wherein the second ends of the hollow fiber filter membranes are potted, thus forming a second potted end, to enable fluid flow from the hollow fiber filter membranes; (b) a constraint that allows the hollow fiber filter membranes to be held in a splayed configuration when in use, sufficient to permit a feed fluid to flow more freely within the interstitial volume between the individual hollow fiber filter membranes, wherein the first potted end and second potted end have first and second surfaces, respectively, from which the fiber filter membranes emerge.

Further disclosed herein is an embodiment of a perfusion filtration module or bioreactor wherein any one of the previously disclosed embodiments, further comprises a protective enclosure to prevent the hollow fiber filter membranes in splayed configuration from being damaged mechanically or electrically during stifling or other motion. The protective enclosure may comprise woven or non woven fabrics, plastics, or metals and may include flexible or rigid screens.

Further disclosed herein is an embodiment of a perfusion filtration module or bioreactor wherein in any one of the previously disclosed embodiments, the first and second surfaces assume a convex shape.

Further disclosed herein is an embodiment of a perfusion filtration module or bioreactor wherein, in the immediately preceding embodiment, when in use, the first ends of the hollow fiber membranes and the second ends of the hollow fiber membranes are mounted or potted so as to emerge from the first and second surfaces, respectively, at angles approximately normal to their respective surfaces.

Further disclosed herein is an embodiment of a perfusion filtration module or bioreactor wherein the first and second surfaces assume the same or different shape, chosen from conical, semispherical, or flat. A flat surface is identifiable as a planar surface. When in use, the first ends of the hollow fiber membranes and the second ends of the hollow fiber membranes may be mounted or potted so as to emerge from the first and second surfaces, respectively, at angles approximately normal to the first and second surfaces.

Further disclosed herein is an embodiment of a perfusion filtration module or bioreactor wherein the hollow fiber filter membranes have a splayed configuration with a degree of splay between 1.1 and 15. Alternatively, the degree of splay may be between 1.2 and 12. Alternatively, the degree of splay may be between 1.5 and 10. Alternatively, the degree of splay may be between 2 and 7. The choice of degree of splay is related to the ability of the fiber filter membrane to bend without buckling. A simple estimate of the degree of splay, tolerable by a certain type of slender fiber may be obtained from Euler's formula, viz.

$$P_{cr} = \frac{\pi^2}{4L^2}EI$$

where $P_{cr}$ is the critical load (in units of pressure), the load at which the fiber will buckle, E is the elastic modulus of the material, I is the moment of inertia of the fiber and L is the length of the fiber. Euler's equation estimates the maximum force per unit area that may be applied to the fiber before buckling occurs.

Further disclosed herein is an embodiment of a perfusion filtration module or bioreactor which further comprises a housing, said housing comprising at least 1 inlet port for admitting feed fluid so as to come into contact with the upstream side of the fiber filter membranes, a manifold, in fluidic contact with the inside lumen of the fiber filter membranes, such that it receives or feeds fluid from or into the inside lumen of the fiber filter membranes, and at least one exit port in fluidic contact with the manifold, as shown in FIG. 5.

As will become evident, various modifications and enhancements of the above embodiments are within the scope of the subject matter disclosed and claimed herein.

The pores in the semi-permeable hollow fiber membrane can range from approximately 0.001 to 100 µm (microns). Further, there are various categories of membrane, depending on the average pore size: microfiltration and ultrafiltration. Microfiltration membranes have pores ranging from approximately 0.1 micrometers to 100 micrometers, while an ultrafiltration membrane has pores ranging from approximately 1 nanometer to 10 micrometers. Such a membrane may also be expressed by its ability to fractionate proteins, nucleic acids and other polymers by size. For example, an ultra-filtration membrane may have a molecular weight cutoff (MWCO) range from 1,000 to 1,000,000 Daltons, pertaining to the approximate molecular weight of the polymer retained by the ultra-filtration membrane.

Suitable materials of construction for hollow fiber filter membranes include, without limitation, hydrophobic materials, hydrophilic materials and amphiphilic materials. In addition, some materials, such as polyamides may display bulk hydrophilic properties and surface hydrophobic properties. Without intending to be bound by theory, the degree of hydrophobicity or hydrophilicity may permit wicking of the carrying solvent through the pores of the filter membrane; thus influencing selectivity, and/or non-specific or amphiphilic binding of the molecules to the membrane.

More specifically, materials of construction may be organic or inorganic with inorganic ceramic filters useful where filtration at extreme temperatures is carried out. Organic materials, such as polymers, may be used at moderate temperatures of about −100° C. to about 300° C. in some cases, although certain organic polymers may be suitable for higher temperature use. Hydrophobic materials of construction include, without limitation, polysulfone, polyethersulfone, polypropylene, polyethylene, polyvinylidene fluoride, hydrophobic poly tetrafluoroethylene (PTFE), hydrophobic polyamides and the like. Hydrophilic materials of construction include, without limitation, polylactic acid and analogous polymerized hydroxy acids, cellulose acetate, mixed cellulose esters, hydrophilic polyamides, and the like. The monomer repeat units of the foregoing polymers may be used in copolymers to adjust polymer physical properties, and to obtain the desired levels of hydrophobicity and hydrophilicity. Such amphiphilic materials may provide the opportunity for greater selectivity. In addition, amphiphilic materials may provide self-organizing properties. For example, it is known that certain block copolymers comprising two or more monomer units that are insoluble in one another can undergo self organization, wherein blocks comprising the monomer units separate from one another and form domains. Such self organized materials are another example of amphiphilic materials. It is further understood that certain of the foregoing polymers may display interesting electrical properties. For example, polyamides, such as the odd nylons, and polyvinylidine fluoride are ferroelectric materials. Such properties may also be useful in filtration applications.

Filter pore structures vary widely. While no limitation is intended, several examples are provided herein. In some applications, it may be advantageous to employ a filter having track-etched pores, which may be formed using some form of radiation such as alpha particles. Track-etched pores have approximately columnar or branched columnar structures. In other applications, filter pores having a fused network structure may be appropriate. Still other applications may benefit from using fibrous pore structures. In other applications, pores may comprise cells or chambers with openings in their walls that allow a fluid to flow between them. Fibrous or non fibrous pore structures may support depth filtration, in which multiple layers of media, or a thicker medium forms a path to retain particles. This type of medium usually retains larger particles at surface level and then finer particles through the layers or thickness. In addition, ceramic materials having sintered pores may be used as long as they can be splayed without breaking them. It is further understood that the structure of the pores is also influenced by the pressure drop across the membrane.

Bundles of hollow fiber membranes, usually having similar diameter and pore size, may be sealed in potting material such that, when in use, the interiors of the fibers are accessible to a fluid manifold without contaminating the permeate on the insides of the fibers. Suitable potting materials include, without limitation, heat and light curable resin formulations, other room temperature curable resin formulations, polymer melts, fusible powders and other encapsulants. Exemplary potting materials include, without limitation, epoxy resins, urethane resins, aminoplast and amidoplast resins, alone or mixed with phenolic or other suitable resins, silicone resins, heat or ultraviolet curable (meth)acrylic resins, polyester resins and hot melt waxes and resins.

Perfusion filtration modules or bioreactors may be modular cartridges wherein the hollow fiber membranes are enclosed in a self-contained module or a larger bioreactor unit may comprise one or more bundles of splayed fiber filter membranes as described herein. In one embodiment, the fluid is removed from the bioreactor and perfusion filtered. In another embodiment, the fluid remains in the bioreactor and is filtered in situ. The latter method may be desirable because the microorganisms in the reaction mixture may be sensitive to temperature or other environmental changes. Depending on the required capacity, perfusion filtration modules or bioreactors may be arranged and fluidly connected in parallel or in series. The filter membrane surface area available for filtration in the cartridge can be calculated by multiplying the surface area of each fiber by the number of fibers sealed the cartridge housing.

Depending on requirements, perfusion filtration modules or bioreactors may be arranged in series or in parallel. The parallel arrangement provides a convenient way to add membrane surface area by adding modules, rather than using larger filtration segments having more fibers. The series arrangement of filtration segments allows staged filtration with less buildup of cells, debris or or gel layers at the filter wall.

The hollow fiber membrane's pores allow biomanufacturing products to be separated from the bulk fluid mixture, which may contain gels, cell debris and whole cells. A biomanufacturing ingredient is a component of the mixture which can be purified or separated by semipermeable membrane filtration. These ingredients include, but are not limited to, biomanufactured products, solutes, buffers, and contaminants. The biomanufactured product may be the molecule of interest with or without byproducts that may be toxic to the organism that manufactures the product. These are separated from the other biomanufacturing ingredients by the filter membrane. Separation of the products can occur by choosing a membrane to retain the product while allowing other ingredients to pass through. Alternatively, the membrane may be chosen to allow the product to permeate through the membrane while retaining the higher molecular weight ingredients, such as aggregates or contaminants larger than the fiber pore size, to be in the retentate. Of further interest is the manufacture of fermented alcoholic products such as beer, wine and other fermented liquids which may be distilled. Micro filtration may be performed in perfusion mode, as described herein, to process and sterilize the fermented product or precursor fluid. The latter would be distilled to increase alcohol content. Sterilizing filtration removes micro organisms and related debris from the product fluid and may usually be accomplished by filtering through membranes having pore sizes below about 0.3 µm. less than or equal to about 0.22 µm and sometimes between 0.01 µm and 0.22 µm.

Without limitation, materials to be filtered may include ionic materials such as salts, acids bases and buffers, amphoteric materials, zwitterions, organic solvents, water, ionic solvents, microcrystals, latex particles, cross-linked polymers, polymers physically associated into aggregates, chemically or physically linked polymer microgels, aggregates of highly cross-linked polymers, emulsified particles, clumps of associating proteins, microbes, cellulosic debris, latex and emulsion particles, clusters and fibers comprising of biological cells and fibers, cell organelle fragments, incompletely dissolved polymers, proteinaceous particles, cellulosic and other polysaccharide particles, flocculating particles, precipitating particles, phase separating liquid systems, salt crystals, particles due to oxidation or reduction processes, pyrogens, cell debris, cell suspensions, food products, particles emanating from the reaction or process vessel itself, and, aggregated therapeutic proteins.

The inner diameters of the hollow fibers, often referred to as the "lumen diameters" may be of any size, and no size limitation is intended. Notwithstanding, it is frequently convenient to select from among commercially available options. Small sized fibers provide higher surface to volume ratios at the possible expense of higher shear rates, increased pressure drops, which, in turn, may affect pump selection and the ability to effect filtration, and slower axial velocity, depending on the fluid viscosity, solids load, and propensity to form gel layers. Fibers having higher inner diameters may allow for faster axial velocity at lower surface to volume ratios when in perfusion flow mode. Inner diameters may range from about 0.1 mm to about 3.0 mm. Within this range, hollow fiber filter membranes may have inner diameters between about 0.5 mm to about 2.0 mm. In particular, inner diameters may be selected from about 0.5 mm, about 0.63 mm, about 0.7 mm, about 0.75 mm, about 1.0 mm, about 1.4 mm, or about 1.9 mm.

The nominal lengths of the hollow fibers may be of any size, and no size limitation is intended. Notwithstanding, it is frequently convenient to select from among commercially available options. Accordingly, lengths of fibers may vary from their nominal values by as much as 2 cm, depending on the configuration of the filtration segment housing and the potting material. Shorter length fibers allow lower inlet pressures to achieve the same axial velocity as compared to longer fibers of the same inner diameter at the possible expense of filtration efficiency. Longer fibers may offer higher filtration efficiency but may require higher inlet pressure and fluids flowing through them will undergo greater pressure drops and higher shear rates than those flowing through shorter fibers having the same inner diameter. When fibers are arranged linearly and approximately in parallel, their lengths will correspond to the length of the filter segment. Fiber lengths may range from about 12.5 cm to about 150 cm. Within this range, hollow fiber filter membranes may be about 20 cm to about 120 cm long. In particular, fiber lengths may be selected from about 30.5 cm (12 in.), about 61 cm (24 in.), or about 104.1 cm (41 in.). Longer filtration channels may be obtained by arranging two or more filter segments such that the retentate channel of one filter segment is fluidly coupled to the input channel of another filter mounted downstream. In this way, longer filtration paths can be achieved using readily available filter components.

Notwithstanding the foregoing, fibers may also reside in flexible housings wherein splayed fibers are mounted. In such a system fibers would be splayed such layed configuration assumes a variety of shapes.

Within this range, such housing may have lengths between about 13 cm (5 in.) and 127 cm (50 in). In particular. Filter segment housings may be selected from about 30.5 cm (12 in.), about 61 cm (24 in.), or about 104.1 cm (41 in.). Longer filtration channels may be obtained by arranging two or more filter segments such that the retentate channel of one filter segment is fluidly coupled to the input channel of another filter mounted downstream. In this way, longer filtration paths can be achieved using readily available filter components. Filter modules of higher capacity may be obtained by fluidly coupling multiple filtration segments in parallel, with the inputs supplied by the same feed.

Within a perfusion filtration module or bioreactor, there may be any number of hollow fiber filter membranes and no numerical limitation is intended. Notwithstanding, it is frequently convenient to select from among commercially available options. Accordingly, a filter segment may have from 1 to about 100,000 hollow fiber membranes, depending on the diameter of the fiber and the dimensions of the filter housing. For example, a 15.2 cm (about 6 inch) inner diameter filter segment housing may have 50,000 or more 0.25 mm hollow fiber membranes within it.

Precision pumps such as metering pumps move a precise volume of liquid in a specified period of time; thus providing an accurate flow rate. In this way, pressure may be applied to assist in regulating permeate flow. Without limitation, pumps may include reciprocating piston pumps, syringe pumps, rotational pumps, gear pumps, peristaltic pumps, diaphragm pumps or the like. Drive motors on the pumps may include electronically driven motors such as stepper motors, pneumatic motors, electric motors or the like. Moreover, the motor may act as a sensor to indicate the level of resistance imposed by the diafiltration system. For example, the electric current of the motor can be monitored to indicate how much work is being done to maintain a given level of permeate flux. Trans membrane pressure may be controlled by controlling the pressure within the reactor.

In addition to pumps, pressure sensors and flow meters may be employed to monitor conditions and maintain process control. Pressure sensors may include, without limitation, diaphragm pressure gauges, capacitive pressure sensors, electromagnetic inductance pressure sensors, piezoelectric, pressure sensors, piezoresistive, pressure sensors, optical pressure sensors potentiometric pressure sensors, MEMS pressure sensors or the like. Flow meters may include, without limitation, mechanical flow meters or electronic flow meters. Mechanical devices include, without limitation, radial turbines, propeller-type turbines, vane type instruments, linear resistance meters, vortex flow meters and the like. Electronic flow meters include, without limitation, ultrasonic Doppler anemometers, laser Doppler anemometers, magnetic flow meters, Coriolis flow meters, and the like. It may be convenient to use different flow and pressure sensing devices when liquids or gases are being processed.

Control of the trans-membrane pressure may be manual or it may be accomplished by electronic control. Manual controls may provide electrical or mechanical engagement such that the pump motors are switched on and off to hold a preset permeate flux tolerance. Simple manual controls may include pinch clamps, switches, capacitive devices or other ways of achieving electrical engagement. In addition, the controller may comprise a logic circuit or a computing device such as a processor, operatively coupled to the controls as well as to sensors, actuators and the like. Actuators, may be employed to engage automatically to control pumps and valves.

Processors may comprise any circuit for performing data processing, including digital signal processors, single processors, parallel processors, analog processors, memory management processors, optical processors, equivalents thereof and combinations thereof. In addition, processors may include auxiliary circuits, either integrated with the processor or in separate devices operating with the processor. Auxiliary circuits may be any circuit that provides an additional function on behalf of the processors and can be shared between two or more processors. Auxiliary circuits may include memories such as semiconductor memories, magnetoresistive memories, disk memories, flash memories, or any equivalent means for storing data. Auxiliary circuits and logic devices may comprise gate arrays, adders, other programmed logic circuits, amplifiers, triggers, A/D converters, D/A converters, optical interfaces, serial and parallel interfaces, buffers, masking circuits, encryption circuits, direct memory access circuits, equivalents thereof or combinations thereof.

Program logic may comprise computer programs written in any known language, such as C, C++, Pearl, Fortran, Basic, Pascal, assembly language, machine language, equivalents thereof or combinations thereof. Program logic may further comprise parallel processing logic for employing multiple processors or processor cores, direct memory access logic for continual monitoring functionality, masked direct memory access, interrupt routines, interrupt service routines, equivalents thereof or combinations thereof.

Table lookup logic may comprise interpolation and extrapolation routines, based on polynomials, spline functions, rational functions, normalized spectral elements, equivalents thereof or combinations thereof. Further, table lookup logic may comprise ordered table searching, searching with correlated values, estimation by neural networks, multidimensional estimation, equivalents thereof or combinations thereof. Data for table lookup may be obtained experimentally.

The processor may gather data using various sensors and other devices, such as pressure sensors, flow sensors, accelerometers, actuators and the like. By monitoring the various inputs, the permeate flux may be adjusted continually in each permeate channel.

Pressure sensors may comprise piezoelectric sensors, piezoresistive sensors, capacitive sensors, which may comprise foams or other elastic materials as well as ceramics and fluids, electromagnetic sensors, in which the physical displacement of a diaphragm or cantilever causes changes in inductance, reluctance or capacitance, a linear variable differential transformer device, Hall effect devices, equivalents thereof or combinations thereof.

Some fluids such as those that contain monoclonal antibodies may exhibit exceptionally high viscosity. Such materials may be prone to concentration polarization of ionic materials, which may further impede fluid flow. Under some circumstances, viscosity lowering excipients may be used. Such materials have a wide range of biophysical-chemical properties. They may modify viscosity, aggregation propensity, or stability. Such excipients include amino acids or their salt forms such as alanine, proline, valine, glycine, serine, histidine (HCl), lysine (HCl), arginine (HCl), and sodium glutamate. In addition, pharmaceutically acceptable salts may be used such as NaCl, NaOAc, $Na_2SO_4$, and $NH_4Cl$. In some embodiments, chaotropic reagents such as urea, imidazole, betaine, or guanidinium chloride may be used. It is understood that the organic materials listed herein as excipients may be employed as salts or as their parent compounds. Suitable pharmaceutically acceptable salts include acid addition salts which may, for example, be formed by reacting a compound of interest with a suitable pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

While sheer rate is less frequently encountered in perfusion filtration, there are some biologically derived products that are extremely sensitive. These include certain biopolymers such as plasma proteins are sensitive to shear rate; which sensitivity has physiological significance. Of such proteins, one example, the von Willebrand factor (VWF), may undergo unfolding at high shear. The unfolded VWF adheres to substrates such as collagen and provides a template for platelet adhesion and eventual clotting of blood. In small blood vessels, an opening such as a wound may result in a high shear situation which, in turn triggers unfolding of VWF and the subsequent clotting response. Within a hollow fiber filter, high velocities may give rise to shear rates that may denature VWF or similar materials. Filtration of folded VWF without damaging it may be accomplished by maintaining the shear rate below 2300 $sec^{-1}$, below 2000 $sec^{-1}$, or below 1800 $sec^{-1}$.

During the perfusion filtration process, a coating of gels, cells and other debris form on the outer walls of the fiber filter membranes, forming a coating. Such coatings may exhibit increased viscosity, relative to the bulk solution, often according to a power law or other function such as a polynomial or supralinear function of concentration. The nature of the function will depend on the particular intermolecular interactions between solvent molecules, solvent and solute molecules, and solute molecules interacting with each other. In one embodiment, the concentration may be collected in the course of uninterrupted flow. Alternatively or in combination, the concentrate may be collected by periodically flushing it from the walls of the membranes, using a back pressure, applied from the permeate compartment by operating the pump(s) in reverse or the feed compartment by operating the feed pumps in reverse, as appropriate, or by applying pressure on the permeate side at a magnitude sufficient to ensure some of the filtrate is going back into the bulk fluid. Further flushing with buffer solution may also serve to dilute the concentrate sufficiently to allow purging of the outer walls of the filter tubes. Within certain limits, it may be possible to promote collection of the filtrate by increasing temperature, although care should be taken to avoid temperature induced denaturation in situations where higher temperatures would cause disruption of hydrogen bonding or other intermolecular or intramolecular interactions.

In certain circumstances, it may be useful to estimate the backflush from the lumen to the outside of the filter fiber. During the backflush, flow velocity depends on fluid parameters such as viscosity, solids loading and the propensity to form gel layers. Accordingly, a priori calculations of the permeate flux may result in estimated values having some level of error. Notwithstanding, control of the backflush flux can be accomplished by varying factors, such as fiber membrane inner diameter, pore size, pore density at the membrane surface, resistance to flow by membrane pore density, and variation of the trans-membrane pressure. The backflush flux may then be monitored empirically. The trans-membrane fluid velocity, v is related to the backflush flux across the membrane, J, in the following way:

$$v = J \cdot A = \frac{\Delta P_{TM} A N_f}{(R_m + R_c)\mu} = \frac{\Delta P_{TM} \pi d^2 l_f N_f}{4(R_m + R_c)\mu}$$

where $\Delta P_{TM}$ represents the trans-membrane pressure, A is the inner area of the hollow fiber membrane, $R_m$ and $R_c$ represent the resistances of the membrane and "cake", respectively, $l_f$ is the length of an individual fiber, $N_f$ represents the number fibers, and $\mu$ is the dynamic viscosity of the fluid within the lumen.

In some cases, the backflush operation may result in flow within the lumen, wherein the resulting shear rate might damage or denature the solute. During the backflush operation, The shear rate of a Newtonian fluid within the hollow fiber filter membranes may be approximated by $$\dot{\gamma} = \frac{169766 \cdot Q}{N_f d^3}$$

where $\dot{\gamma}$ is shear rate, Q represents the backflush trans-membrane flow rate of the fluid into the lumen in liters/min, $N_f$ is the number of fibers in the bundle and d is the inner diameter of the fibers in mm. The constant, 169,766, may be regarded as a suitable first approximation but may be refined using empirical data for a given system. The resulting stress attributable to the shear rate is given by $$\tau_w = \dot{\gamma}\mu$$

where $\tau_w$ represents the shear stress, and $\mu$ represents the dynamic viscosity of the fluid within the lumen.

For the purposes of process control, it may be useful to model the axial velocity $u_x$, of the fluid within an individual lumen, either in forward or backflush mode. For a Newtonian fluid, $u_x$ may be modeled by the following equation:

$$u_x = \frac{21.22 \cdot Q}{d^2 N_f}$$

wherein the variables are as defined, supra. As above, the constant, 21.22 may serve as a reasonable first approximation, which may be refined using experimental data. Alternatively, $u_x$ may be measured empirically using Doppler ultrasound measurements if the lumen diameter is sufficiently large. Both $\tau_w$ and $u_x$ may be controlled using pressure control valves or regulators, flow control valves, pumps, or other standard control equipment known in the art. In one embodiment, a perfusion module may be configured and operated such that the shear rate is maintained below 2300 $sec^{-1}$, below 2000 $sec^{-1}$, or below 1800 $sec^{-1}$. In another embodiment, a perfusion module may be configured and operated such that the shear rate is maintained above 2300 sec$^{-1}$, above 3000 sec$^{-1}$, or above 3500 sec$^{-1}$.

The filtration segment inner diameter refers to the inner diameter or equivalent inner dimension of the filter housing, wherein the hollow fibers reside and should have the inner diameter to accommodate the required degree of splay. No limitation is implied on a module inner diameter. Notwithstanding, aqueous filters for biological systems, for example, may be conveniently chosen to have filtration segment inner diameters between about 0.5 cm and about 26 cm. As a further example, filtration segment inner diameters may be chosen to be between about 0.95 cm and about 16 cm.

One advantage of the various embodiments disclosed herein is that a backwash process can easily be used to clean the filter fibers of cells, gels and debris so that permeability can be at least partially restored. Backwashing may be accomplished by urging a clean solution such as, without limitation, a buffer solution or a quantity of permeate from the lumens to the outsides of the filter fibers. This may be accomplished with or without temperature modification, pulsing or ultrasonic assistance as required.

Although the present invention has been shown and described with reference to particular examples, various changes and modifications which are obvious to persons skilled in the art to which the invention pertains are deemed to lie within the spirit, scope and contemplation of the subject matter set forth in the appended claims.

We claim:

1. A perfusion filtration module for filtering a feed fluid, comprising:
   a. a fiber array comprising a plurality of hollow fiber filter membranes, each having a first end and a second end, wherein the first ends of the hollow fiber filter membranes are potted, thus forming a first potted end, to enable filtrate flow from the hollow fiber filter membranes, and wherein the second ends of the hollow fiber filter membranes are either:
      i. potted, thus forming a second potted end, to enable fluid flow from the hollow fiber filter membranes; or alternatively
      ii. mounted, thus forming a mounted end, so that the hollow fiber filter membranes are sealed to prevent filtrate flow;
   b. a constraint that allows the hollow fiber filter membranes to be held in a splayed configuration, wherein:
      i. the first potted end and the second potted end, or alternatively, the first potted end and the mounted end, comprise first and second surfaces, respectively, from which the fiber filter membranes emerge, and
      ii. a housing, and the first potted ends and the second potted ends, or the mounted ends, of the plurality of hollow fiber filter membranes are fixed relative to the housing;
   wherein the splayed configuration is a configuration in which the hollow fiber filter membranes spread out from one another as they extend away from the first potted end and the second potted end, or the mounted end, to increase an interstitial distance between adjacent ones of the plurality of hollow fiber filter membranes across a width of the perfusion filtration module between the first potted end and the second potted end, or the mounted end, and
   wherein the splayed configuration has a degree of splay and the degree of splay is greater than 1, wherein the degree of splay is the relative amount of splay expressed as a ratio of the maximum lateral dimension of the splayed fiber array to the lateral dimension of the fiber array when stretched in its maximum lineal dimension.

2. The perfusion filtration module of claim 1, further comprising a protective enclosure to prevent the hollow fiber filter membranes in splayed configuration from being damaged during stirring or other motion.

3. The perfusion filtration module of claim 2, wherein the protective enclosure is metal or plastic, comprising woven or non-woven fabrics, plastics, or metals.

4. The perfusion filtration module of claim 1, wherein the first and second surfaces are flat.

5. The perfusion filtration module of claim 1, wherein the first and second surfaces are planar.

6. The perfusion filtration module of claim 5, wherein when in use, the first ends of the hollow fiber membranes and the second ends of the hollow fiber membranes are mounted or potted so as to emerge from the first and second surfaces, respectively, at angles approximately normal to the first and second surfaces.

7. The perfusion filtration module of claim 5, wherein the degree of splay is between 1.1 and 15.

8. The perfusion filtration module of claim 5, wherein the degree of splay is between 1.2 and 12.

9. The perfusion filtration module of claim 5, the degree of splay is between 1.5 and 10.

10. The perfusion filtration module of claim 5, the degree of splay is between 1.5 and 8.

11. The perfusion filtration module of claim 5, the degree of splay is between 2 and 7.

12. The perfusion filtration module of claim 5, wherein the degree of splay bends the fiber filter without buckling.

13. The perfusion filtration module of claim 1, further comprising a housing, said housing comprising at least 1 inlet port for admitting feed fluid so as to come into contact with the upstream side of the fiber filter membranes, a manifold, in fluidic contact with the inside of the fiber filter membranes, such that it receives or feeds fluid from or into the inside of the fiber filter membranes, and at least one exit port in fluidic contact with the manifold.

14. The perfusion filtration module of claim 1, wherein the perfusion filtration module comprises a rod holding the potted first ends and the second potted ends, or the mounted ends, such the hollow fiber filters may be in the splayed configuration.

15. The perfusion filtration module of claim 1, further comprising a pressure control valve to regulate vacuum, such that the shear rate is maintained below 2300 sec$^{-1}$.

16. A membrane bioreactor comprising a perfusion filtration module for filtering a feed fluid, said perfusion filtration module comprising:
   a. a fiber array comprising a plurality of hollow fiber filter membranes, each having a first end and a second end, wherein the first ends of the hollow fiber filter membranes are potted, thus forming a first potted end, to enable filtrate flow from the hollow fiber filter membranes, and wherein the second ends of the hollow fiber filter membranes are either:
      i. potted, thus forming a second potted end, to enable fluid flow from the hollow fiber filter membranes; or alternatively
      ii. mounted, thus forming a mounted end, so that the hollow fiber filter membranes are sealed to prevent filtrate flow;
   b. a constraint that allows the hollow fiber filter membranes to be held in a splayed configuration, wherein:

i. the first potted end and the second potted end, or alternatively the first potted end and the mounted end, comprise first and second surfaces, respectively, from which the fiber filter membranes emerge, and c. a housing, and the first potted ends and the second potted ends, or the mounted ends, of the plurality of hollow fiber filter membranes are fixed relative to the housing;

wherein the splayed configuration is a configuration in which the hollow fiber filter membranes spread out from one another as they extend away from the first potted end and the second potted end, or the mounted end, to increase an interstitial distance between adjacent ones of the plurality of hollow fiber filter membranes across a width of the perfusion filtration module between the first potted end and the second potted end, or the mounted end, and wherein the splayed configuration has a degree of splay and the degree of splay is greater than 1, wherein the degree of splay is the relative amount of splay expressed as a ratio of the maximum lateral dimension of the splayed fiber array to the lateral dimension of the fiber array when stretched in its maximum lineal dimension.

* * * * *